US006200731B1

(12) United States Patent
Lee et al.

(10) Patent No.: US 6,200,731 B1
(45) Date of Patent: Mar. 13, 2001

(54) PHOTORESIST CROSS-LINKING MONOMERS, PHOTORESIST POLYMERS AND PHOTORESIST COMPOSITIONS COMPRISING THE SAME (75) Inventors: Geun Su Lee; Cha Won Koh; Jae Chang Jung; Min Ho Jung; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/465,112

(22) Filed: Dec. 16, 1999

(30) Foreign Application Priority Data

Dec. 31, 1998 (KR) .................................. 98-63794

(51) Int. Cl.$^7$ ............................. G03C 1/73; G03F 7/213; G03F 7/30; C08F 32/06; C08F 34/02; C08F 34/04; C07C 69/753

(52) U.S. Cl. ...................... 430/270.1; 430/325; 430/326; 430/914; 526/256; 526/268; 526/281; 549/57; 549/463; 560/118; 560/120

(58) Field of Search .................................. 526/256, 268, 526/281; 549/57, 463; 560/118, 120; 430/270.1, 325, 326, 319, 914

(56) References Cited

U.S. PATENT DOCUMENTS

| | | | |
|---|---|---|---|
| 3,869,502 | * 3/1975 | Papa et al. | 560/120 |
| 3,966,797 | * 6/1976 | Colomb, Jr. et al. | 560/115 |
| 4,352,939 | 10/1982 | Paucot | 560/120 |
| 4,707,301 | * 11/1987 | Lange | 508/426 |

* cited by examiner

Primary Examiner—Janet Baxter
Assistant Examiner—Sin J. Lee (74) Attorney, Agent, or Firm—Townsend and Townsend and Crew LLP (57) ABSTRACT

The present invention discloses a cross-linking monomer for a photoresist polymer represented by following Chemical Formula 1:

<Chemical Formula 1>

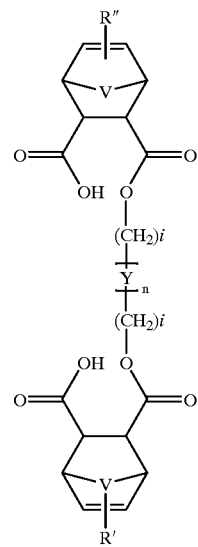

wherein, V represents $CH_2$, $CH_2CH_2$, oxygen or sulfur; Y is selected from the group consisting of straight or branched $C_{1-10}$ alkyl, oxygen, and straight or branched $C_{1-10}$ ether; R' and R" individually represent H or $CH_3$; i is a number of 1 to 5; and n is a number of 0 to 3; and a process for preparing a photoresist copolymer comprising the same.

19 Claims, 2 Drawing Sheets

PHOTORESIST CROSS-LINKING MONOMERS, PHOTORESIST POLYMERS AND PHOTORESIST COMPOSITIONS COMPRISING THE SAME

FIELD OF THE INVENTION

The present invention relates to cross-liking monomers for photoresist polymers, photoresist polymers and photoresist compositions comprising the same. More specifically, it relates to cross-linking monomers which can noticeably improve the polymerization yield of photoresist copolymers, and a process for preparing a photoresist copolymer using the same.

BACKGROUND OF THE INVENTION

Recently, photoresist copolymers wherein alicyclic monomers have been introduced into the main chain or branched chain have proven to be useful to obtain ultra-micro patterns. However, photoresist copolymers consisting of alicyclic monomers typically have a low polymerization yield, thereby synthesis of the copolymer requires high production cost.

In addition, as the amount of the monomer employed in the polymerization increases, the polymerization yield is noticeably lowered, so that the photoresist polymer can be hardly prepared on a large scale.

SUMMARY OF THE INVENTION

The object of the present invention is to solve the problems described above, and to provide cross-linking monomers which can reduce the production cost of photoresist polymers by maximizing their polymerization yield and thereby make mass production of such polymers possible.

Another object of the present invention is to provide photoresist polymers using said cross-linking monomers, and processes for the preparation thereof.

Still another object of the present invention is to provide a photoresist composition using the photoresist polymer described above, which is usable in a lithography process employing an extremely short wavelength light source.

DETAILED DESCRIPTION OF THE INVENTION

In order to achieve the object described above, the present invention provides a cross-linking monomer represented by following Chemical Formula 1:

<Chemical Formula 1> wherein, V represents $CH_2$, $CH_2CH_2$, oxygen or sulfur; Y is selected from the group consisting of straight or branched $C_{1-10}$ alkyl, oxygen, and straight or branched $C_{1-10}$ ether; R' and R" individually represent H or $CH_3$; i is a number from 1 to 5; and n is a number from 0 to 3.

To achieve another object of the present invention, a photoresist copolymer is provided which uses the cross-linking monomer represented by Chemical Formula 1 as a comonomer.

In addition, a photoresist composition is provided which comprises (i) a photoresist copolymer as described above, (ii) a photoacid generator, and (iii) an organic solvent.

Synthesis of Cross-linking Monomers for Photoresist Polymers

The inventors have performed intensive studies to achieve the objects of the invention described above, and found that a compound represented by Chemical Formula 1 improves the polymerization yield of polymers by making the photoresist polymers cross-link to one another. The cross-linking monomer according to the present invention is particularly effective to improve the polymerization yield of a copolymer having an alicyclic olefin main chain.

The properties of cross-linking monomers represented by Chemical Formula 1 are described hereinbelow:

(1) The cross-linking monomer comprises alicyclic compounds including double bonds therein. In the polymerization process, the double bonds are broken to induce cross-linking with other comonomers participating in the polymerization, thereby resulting in higher polymerization yield.

(2) Since one cross-linking monomer molecule has two carboxylic groups, it can properly adjust the solubility difference in the developing solution between the exposed area and the unexposed area during the developing step of the photolithography process.

(3) Since the alicyclic structure of the cross-linking monomer constitutes the main chain of the photoresist polymer, a photoresist polymer having excellent etching resistance can be obtained.

(4) Since the cross-linking monomer has two carboxyl groups, which are hydrophilic and have an affinity for silicon, excellent adhesiveness between the photoresist pattern and the substrate can be retained. Thus, breakdown of the pattern can be prevented when forming a pattern of high integrity, thereby allowing a highly reliable semiconductor element to be manufactured.

(5) In the case where a photoresist polymer is prepared by copolymerization of a monomer having free hydroxyl group(s) with maleic anhydride, there have been some problems with storage stability of the polymer because the hydroxyl group is apt to react with the maleic anhydride. However, by using the cross-linking monomer according to the present invention, the reaction of the hydroxyl group with maleic anhydride can be avoided by the cross-linkage, so that storage stability of the resulting polymer can be improved.

(6) In addition, cross-linking monomers of the present invention are odorless and can be easily synthesized in a pure state by crystallization from a mixed organic solvent (for example, benzene/hexane), without employing complicated separation steps such as distillation or column chromatography.

Synthesis of Photoresist Polymers

The photoresist copolymers according to the present invention are prepared by adding a cross-linking monomer of Chemical Formula 1 to other photoresist monomers in the process for synthesizing a conventional photoresist copolymer.

In particular, a cross-linking monomer according to the present invention is useful for improving the polymerization yield of alicyclic monomers when a photoresist copolymer is prepared by dissolving one or more alicyclic monomers in organic solvent, adding a cross-linking monomer represented by Chemical Formula 1, and then adding a radical polymerization initiator or metal catalyst to the resultant mixture to induce polymerization.

Bulk polymerization or solution polymerization may be employed as a polymerization process. As the polymerization initiator, 2,2-azobisisobutyronitrile (AIBN), benzoylperoxide, acetylperoxide, laurylperoxide, t-butyloxide, bis-azide type compounds, or the like may be used. Tetrahydrofuran, dimethylformamide, chloroform, ethyl acetate, acetone, ethyl methyl ketone, benzene, toluene, xylene, or the like may be used as the polymerization solvent. Tetrahydrofuran, dioxane or dimethylformamide are the most preferred polymerization solvents. If the polymer is to be obtained, the polymer as a solid, diethyl ether, petroleum ether, n-hexane, cyclohexane, methanol, ethanol, propanol or isopropyl alcohol may be used as the polymerization solvent, with diethyl ether, petroleum ether or n-hexane being the most preferred.

The polymerization process according to the present invention is carried out at a temperature between 50° C. to 120° C., preferably 50° C. to 80° C. under a nitrogen or argon atmosphere for 4 to 24 hours. However, the invention is not restricted to such polymerization conditions.

The photoresist copolymer prepared by above process preferably comprises (i) an alicyclic compound having an acid labile group, as the first comonomer, (ii) a cross-linking monomer according to the present invention, as the second comonomer and (iii) maleic anhydride and/or a compound represented by Chemical Formula 16 as the third comonomer:

<Chemical Formula 16> wherein, Z represents $CH_2$, $CH_2CH_2$, oxygen or sulfur.

As the acid labile group, tert-butyl, 2-tetrahydropiranyl, 2-tetrahydrofuranyl, or the like may be used.

Maleic anhydride makes the bondings between each comonomer strong, and properly adjusts the molecular weight of the polymer (preferably 14,000 to 30,000) to contribute to the increase in polymerization ratio. In addition, the polymerization is further facilitated by adding the compound represented by Chemical Formula 16 since the compound prevents steric hindrance between large pendant groups of the first and second monomers.

Preferred photoresist polymers prepared by using the polymerization process of the present invention are represented by following Chemical Formula 17:

<Chemical Formula 17> wherein, Z, W, and V individually represent $CH_2$, $CH_2CH_2$, oxygen or sulfur; R represents an acid labile group; Y is selected from the group consisting of straight or branched $C_{1-10}$ alkyl, oxygen, and straight or branched $C_{1-10}$ ether ; R' and R" individually represent H or $CH_3$, n is a number from 0 to 3, i is a number from 1 to 5, and a, b, c, and d individually represent the polymerization ratio of each comonomer participating in the polymerization. The ratio a:b:c:d is preferably is 50%:0–30 mol %:10–40 mol %:0.1–10 mol %.

The molecular weight of the preferred photoresist polymers of the present invention are in a range of 3,000 to 30,000.

Synthesis of Photoresist Compositions

A photoresist composition may be prepared in accordance with the present invention by mixing in organic solvent a photoresist copolymer represented by Chemical Formula 17 and a photoacid generator. As a photoacid generator, a sulfide or onium type compound, for example, diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate or dibutylnaphthylsulfonium triflate may be used. The amount of the photoacid generator is preferably 0.05 to 10% by weight based on the photoresist polymer. If the amount is less than 0.05% by weight, photosensitivity of the photoresist is poor. If the amount is 10% or more, a pattern having poor profile is obtained because the photoacid generator absorbs too much ultraviolet light.

As an organic solvent, ethyl 3-ethoxypropionate, methyl 3-methyoxypropionate, cyclohexanone, propylene glycol methyl ether acetate, cyclopentanone or other conventional organic solvent may be used. The amount of solvent used is preferably 200 to 1000% by weight of the photoresist polymer. According to experiments by the inventors, it has been found that when the amount of solvent is 600% by weight, a photoresist film having a thickness 0.5 μm can be obtained.

A process for forming a photoresist pattern using a photoresist composition of the present invention, is described below:

First, a photoresist composition according to the present invention is spin-coated on a silicon wafer to form a thin photoresist film thereon, which is then "soft-baked," and then exposed to patterned light by using a deep ultraviolet exposer or an excimer laser exposer. ArF, KrF, VUV, EUV E-beam, x-ray or the like may be used as the light source, and the energy of light exposure is preferably from 1 to 30 mJ/cm².

Then, the thin photoresist film is "post-baked" at 70° C. to 200° C. for about 1 to 2 minutes, and the photoresist film was developed in alkaline developing solution, for example, aqueous TMAH (tetramethylammonium hydroxide) solution, to obtain micro-pattern of 0.15 μm or less.

A cross-linking monomer according to the present invention increases polymerization ratio by forming cross-links between the comonomers participating in the polymerization. Thus, the photoresist copolymer can be produced on a large scale with low production cost.

DETAILED DESCRIPTION OF PREFERRED EMBODIMENT

The invention is described in more detail by referring to the examples below, but it should be noted that the present invention is not restricted to these examples.

Example 1

Synthesis of ethylene glycol di(5-norbornene-2-carboxylic acid-3-carboxylate)

Ethylene glycol (0.1 mole) was added to tetrahydrofuran (100 ml). After stirring the mixture, 5-norbonene-2,3-dicarboxylic anhydride (0.2 mole) was added thereto, and the resultant mixture was stirred until complete dissolution. Sulfuric acid (0.1 ml) was slowly added thereto, and the mixture was reacted at room temperature for 48 hours. After the reaction was completed, tetrahydrofuran was distilled off. The residual solution was extracted with 500 ml of ethyl acetate, dried over MgSO₄, and filtered. The filtrate was evaporated in vacuo to obtain the crude product as a white solid, which was then recrystallized from acetone/petroleum ether, to obtain the compound of Chemical Formula 2 in a pure state (34 g/yield: 95%).

<Chemical Formula 2>

Example 2

Synthesis of 1,3-propanediol-di(5-norbornene-2-carboxylic acid-3-carboxylate)

The synthesis and work-up procedure according to Example 1 was repeated but using 1,3-propanediol instead of ethylene glycol, to obtain the compound of Chemical Formula 3 as a colorless solid (35.7 g/yield: 96%).

<Chemical Formula 3>

Example 3

Synthesis of 1,4-butanediol-di(5-norbornene-2-carboxylic acid-3-carboxylate)

The procedure of Example 1 was repeated but using 1,4-butanediol instead of ethylene glycol, to obtain the compound of Chemical Formula 4 as a colorless solid (36.3 g/yield: 94%).

<Chemical Formula 4>

Example 4

Synthesis of 1,5-pentanediol-di(5-norbornene-2-carboxylic acid-3-carboxylate)

The procedure of synthesis and work-up according to Example 1 was repeated but using 1,5-pentanediol instead of ethylene glycol as a reactant, to obtain the compound of Chemical Formula 5 as a colorless solid (36.8 g/yield: 92%).

<Chemical Formula 5>

Example 5

Synthesis of 2,2-dimethyl-1,3-propanediol-di(5-norbornene-2-carboxylic acid-3-carboxylate)

The procedure of Example 1 was repeated but using 2,2-dimethyl-1,3-propanediol instead of ethylene glycol, to obtain the compound of Chemical Formula 6 as a colorless solid (38.8 g/yield: 97%).

<Chemical Formula 6>

Example 6

Synthesis of 2,2-diethyl-1,3-propanediol-di(5-norbornene-2-carboxylic acid-3-carboxylate)

The procedure of Example 1 was repeated but using 2,2-diethyl-1,3-propanediol instead of ethylene glycol, to obtain the compound of Chemical Formula 7 as a colorless solid (41.5 g/yield: 97%).

<Chemical Formula 7>

Example 7

Synthesis of diethylene glycol-di(5-norbornene-2-carboxylic acid-3-carboxylate)

The same synthesis and work-up procedure according to Example 1 was repeated but using diethylene glycol instead of ethylene glycol, to obtain the compound of Chemical Formula 8 as a colorless solid (36.6 g/yield: 91%).

<Chemical Formula 8>

Example 8

Synthesis of ethylene glycol di(oxabicyclo[2.2.1]oct-5-ene-2-carboxylic acid-3-carboxylate)

Ethylene glycol (0.1 mole) was added to tetrahydrofuran (100 ml). After stirring the mixture, exo-3,6-epoxy-1,2,3,6-tetrahydrophthalic anhydride (0.2 mole) was added thereto, and the resultant mixture was stirred until complete dissolution. To the solution, sulfuric acid (0.1 ml) was slowly added, and the mixture was reacted at room temperature for 24 hours. After the reaction was completed, tetrahydrofuran was distilled off. The residual solution was extracted with 500 ml of ethyl acetate, dried over $MgSO_4$, and filtered. The filtrate was evaporated in vacuo to obtain the crude product as a white solid, which was then recrystallized from acetone/petroleum ether, to obtain the compound of Chemical Formula 9 in a pure state (34.2 g/yield: 95%).

<Chemical Formula 9>

Example 9

Synthesis of 1,3-propanediol-di(oxabicyclo[2.2.1]oct-5-ene-2-carboxylic acid-3-carboxylate)

The procedure of Example 8 was repeated but using 1,3-propanediol instead of ethylene glycol, to obtain the compound of Chemical Formula 10 as a colorless solid (35.2 g/yield: 94%).

<Chemical Formula 10>

Example 10

Synthesis of 1,4-butanediol-di(oxabicyclo[2.2.1]oct-5-ene-2-carboxylic acid-3-carboxylate)

The procedure of Example 8 was repeated but using 1,4-butanediol instead of ethylene glycol, to obtain the compound of Chemical Formula 11 as a colorless solid (36.1 g/yield: 93%).

<Chemical Formula 11>

Example 11

Synthesis of 1,5-pentanediol-di(oxabicyclo[2.2.1]oct-5-ene-2-carboxylic acid-3-carboxylate)

The procedure of Example 8 was repeated but using 1,5-pentanediol instead of ethylene glycol, to obtain the compound of Chemical Formula 12 as a colorless solid (36.2 g/yield: 90%).

<Chemical Formula 12>

Example 12

Synthesis of 2,2-dimethyl-1,3-propanediol-di(oxabicyclo[2.2.1]oct-5-ene-2-carboxylic acid-3-carboxylate)

The procedure of Example 8 was repeated but using 2,2-dimethyl-1,3-propanediol instead of ethylene glycol, to obtain the compound of Chemical Formula 13 as a colorless solid (38.6 g/yield: 96%).

<Chemical Formula 13>

Example 13

Synthesis of 2,2-diethyl-1,3-propanediol-di(oxabicyclo[2.2.1]oct-5-ene-2-carboxylic acid-3-carboxylate)

The procedure of Example 8 was repeated but using 2,2-diethyl-1,3-propanediol instead of ethylene glycol, to obtain the compound of Chemical Formula 14 as a colorless solid (41.3 g/yield: 96%).

<Chemical Formula 14>

Example 14

Synthesis of diethylene glycol-di(oxabicyclo[2.2.1]oct-5-ene-2-carboxylic acid-3-carboxylate)

The procedure of Example 8 was repeated but using diethylene glycol instead of ethylene glycol, to obtain the compound of Chemical Formula 15 as a colorless solid (35.2 g/yield: 87%).

<Chemical Formula 15>

Example 15

Synthesis of poly[ethylene glycol di(5-norbornene-2-caboxylic acid-3-carboxylate)/maleic anhydride/norbornene/t-butyl-5-norbornene-2-carboxylate]

Ethylene glycol di(5-norbonene-2-carboxylic acid-3-carboxylate) (10 mmol), maleic anhydride (100 mmol), norbornene (20 mmol), t-butyl-5-norbornene-2-carboxylate (70 mmol) and AIBN (0.30 g) were dissolved in 25 ml of tetrahydrofuran, and the mixture was reacted at 65° C. for 10 hours. After the reaction was completed, the reaction mix- ture was poured into petroleum ether to obtain a pure solid, which was then filtered and dried to obtain the compound of Chemical Formula 18 (17.9 g/yield: 62%).
<Chemical Formula 18>

Example 16

Synthesis of poly[1,3-propanediol-di(5-norbornene-2-caboxylic acid-3-carboxylate)/maleic anhydride/norbornene/t-butyl-5-norbornene-2-carboxylate]

The procedure of Example 15 was repeated but using 1,3-propanediol-di(5-norbornene-2-carboxylic acid-3-carboxylate) instead of ethylene glycol di(5-norbornene-2-carboxylic acid-3-carboxylate) to obtain the compound of Chemical Formula 19 as a colorless solid (18.9 g/yield: 65%).
<Chemical Formula 19>

Example 17

The photoresist copolymer obtained from Example 15 (10 g) and triphenylsulfonium triflate (0.12 g) as a photoacid generator were dissolved in ethyl 3-ethoxypropionate solvent (60 g), and the resultant mixture was filtered through a 0.10 μm filter to prepare a photoresist composition.

Figure 1:
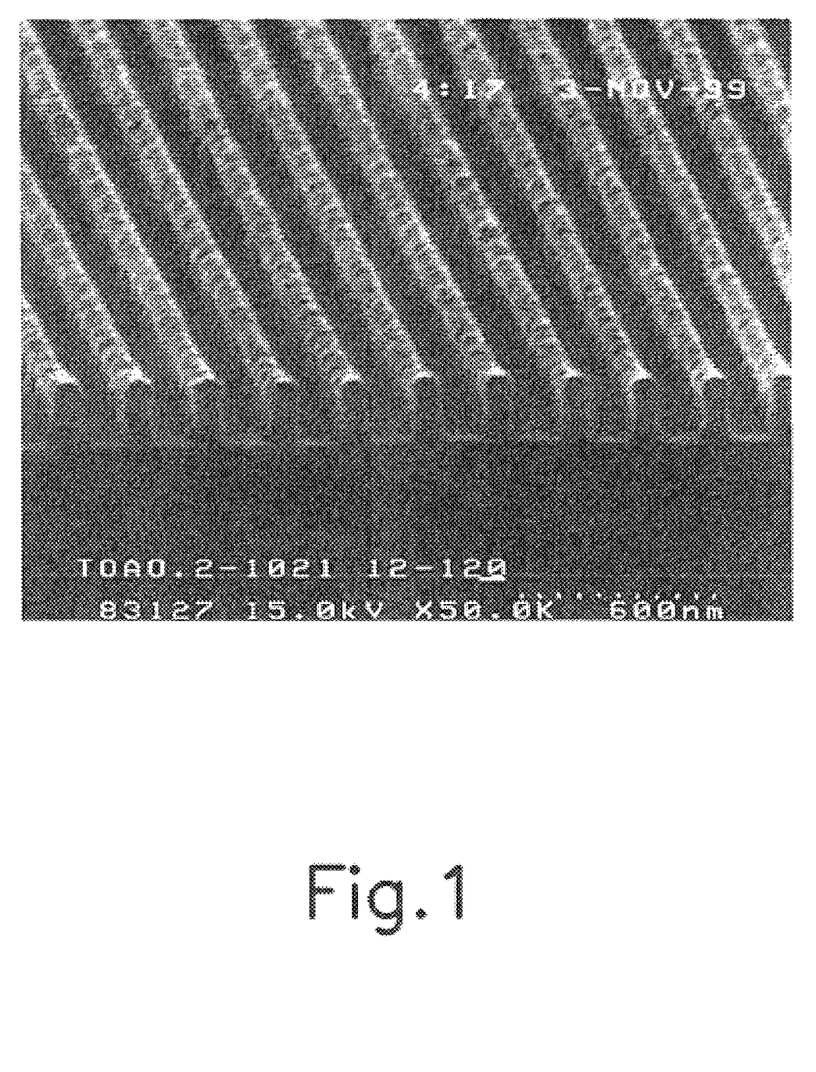
FIG. 1 shows a photoresist pattern obtained from Example 17.

The photoresist composition (1 ml) thus prepared was spin-coated on a silicon wafer, and soft-baked at 110° C. for 90 seconds. After baking, it was exposed to light by using an ArF laser exposer, and post-baked again at 10° C. for 90 seconds. When the post-baking was completed, it was developed in 2.38 wt % aqueous TMAH solution for 40 seconds, to obtain a 0.13 μm L/S pattern (FIG. 1).

Example 18

The procedure according to Example 17 was repeated but using a photoresist copolymer obtained from Example 16 (10 g), to prepare a photoresist composition.

Figure 2:
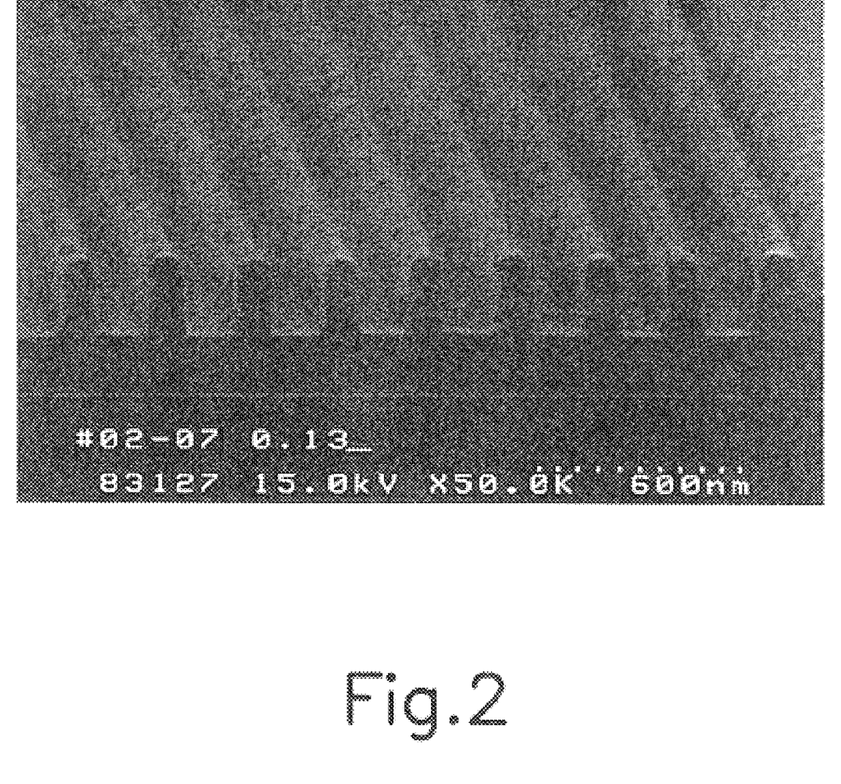
FIG. 2 shows a photoresist pattern obtained from Example 18.

The photolithography procedure of Example 17 was repeated by using the photoresist composition thus prepared, to obtain a 0.13 μm L/S pattern (FIG. 2).

What is claimed is:

1. A cross-linking monomer for a photoresist polymer represented by following Chemical Formula 1:
<Chemical Formula 1> wherein, V represents $CH_2$, $CH_2CH_2$, oxygen or sulfur; Y is selected from the group consisting of straight or branched $C_{1-10}$ alkyl, oxygen, and straight or branched $C_{1-10}$ ether; R' and R" individually represent H or $CH_3$; i is a number from 1 to 5; and n is a number from 0 to 3.

2. A cross-linking monomer according to claim 1 selected from the group consisting of ethylene glycol di(5-norbornene-2-carboxylic acid-3-carboxylate), 1,3-propanediol-di(5-norbornene-2-carboxylic acid-3-carboxylate), 1,4-butanediol-di(5-norbornene-2-carboxylic acid-3-carboxylate), 1,5-pentanediol-di(5-norbonene-2-carboxylic acid-3-carboxylate), 2,2-dimethyl-1,3-propanediol-di(5-norbonene-2-carboxylic acid-3-carboxylate), 2,2-diethyl-1,3-propanediol-di(5-norbonene-2-carboxylic acid-3-carboxylate), diethylene glycol-di(5-norbornene-2-carboxylic acid-3-carboxylate), ethylene glycol di(oxabicyclo[2.2.1]oct-5-ene-2-carboxylic acid-3-carboxylate), 1,3-propanediol di(oxabicyclo[2.2.1]oct-5-ene-2-carboxylic acid-3-carboxylate), 1,4-butanediol di(oxabicyclo[2.2.1]oct-5-ene-2-carboxylic acid-3- carboxylate), 1,5-pentanediol-di(oxabicyclo[2.2.1]oct-5-ene-2-carboxylic acid-3-carboxylate), 2,2-dimethyl-1,3-propanediol di(oxabicyclo[2.2.1]oct-5-ene-2-carboxylic acid-3-carboxylate), 2,2-diethyl-1,3-propanediol di(oxabicyclo[2.2.1]oct-5-ene-2-carboxylic acid-3-carboxylate), and diethylene glycol-di(oxabicyclo[2.2.1]oct-5-ene-2-carboxylic acid-3-carboxylate).

3. A photoresist copolymer comprising a cross-linking monomer according to claim 1.

4. A photoresist copolymer which comprises (i) one or more alicyclic monomers(s) and (ii) a cross-linking monomer according to claim 1.

5. A photoresist copolymer which comprises (i) an alicyclic monomer having an acid labile group, as a first comonomer, and (ii) a cross-linking monomer according to claim 1 as a second comonomer.

6. A photoresist copolymer according to claim 5, which comprises (iii) maleic anhydride and/or one or more compound(s) represented by Chemical Formula 16, as an additional comonomer:
<Chemical Formula 16> wherein, Z represents $CH_2$, $CH_2CH_2$, O or S.

7. A photoresist copolymer according to claim 5 represented by following Chemical Formula 17:
<Chemical Formula 17> wherein, Z, W, and V individually represent $CH_2$, $CH_2CH_2$, oxygen, or sulfur; R represents an acid labile group; Y is selected from the group consisting of straight or branched $C_{1-10}$ alkyl, oxygen, and straight or branched $C_{1-10}$ ether; R' and R" individually represent H or $CH_3$; n represents a number from 0 to 3; i represents a number from 1 to 5; and a, b, c, and d individually represent polymerization ratio of each comonomer participating in the polymerization.

8. A copolymer according to claim 7 wherein the molecular weight is 3,000 to 30,000.

9. A copolymer according to claim 7 wherein the ratio a:b:c:d is 50 mol %:1–30 mol %:10–40 mol %:0.1–10 mol %.

10. A copolymer according to claim 7 selected from the group consisting of poly[ethylene glycol di(5-norbornene-2-carboxylic acid-3-carboxylate)/maleic anhydride/norbornene/tert-butyl-5-norbornene-2-carboxylate] and poly[1,3-propanediol-di(5-norbornene-2-carboxylic acid-3-carboxylate)/maleic anhydride/norbornene/tert-butyl-5-norbornene-2-carboxylate].

11. A process for preparing a photoresist copolymer, which comprises the steps of (a) dissolving one or more alicyclic monomer(s) and a cross-linking monomer according to claim 1 in an organic solvent, and (b) adding a polymerization initiator to the resultant solution to induce a polymerization reaction.

12. A process according to claim 11, wherein the polymerization solvent is selected from the group consisting of tetrahydrofuran, dimethylformamaide, dimethylsulfoxide, dioxane, benzene, toluene and xylene.

13. A process according to claim 11, wherein the polymerization initiator is selected from the group consisting of 2,2-azobisisobutyronitrile(AIBN), benzoylperoxide, acetylperoxide, laurylperoxide, t-butyloxide, and bis-azide type compounds.

14. A process according to claim 11, wherein step (b) is performed at 50° C. to 120° C. under nitrogen or argon atmosphere.

15. A photoresist composition comprising (i) a photoresist copolymer comprising a cross-linking monomer according to claim 1, (ii) a photoacid generator, and (iii) an organic solvent.

16. A process for forming a photoresist pattern, which comprises the steps of (a) coating a photoresist composition according to claim 15 on a wafer, (b) exposing the wafer to patterned light by employing an exposer, and (c) developing the exposed wafer.

17. A process according to claim 16, which further comprises baking step(s) before and/or after step (b).

18. A process according to claim 16, wherein step (b) is carried out by using an ArF (193 nm), KrF (248 nm), VUV (157 nm), EUV (13 nm), E-beam, or X-ray light source.

19. A process according to claim 16, wherein step (c) is carried out using alkaline developing solution.

* * * * *